United States Patent [19]

Yelnosky et al.

[11] 4,198,409

[45] Apr. 15, 1980

[54] TRIAZINONES FOR VETERINARY USE

[75] Inventors: John Yelnosky, Warrington; George H. Douglas, Malvern; Ghulam N. Mir, Buckingham; Dahyabhai M. Patel, Ambler; Chong M. Won, Warrington; Ronald L. Alioto, Havertown, all of Pa.

[73] Assignee: William H. Rorer, Inc., Fort Washington, Pa.

[21] Appl. No.: 959,859

[22] Filed: Nov. 13, 1978

[51] Int. Cl.$^2$ .................... A61K 31/53; A61K 31/54; A61K 31/535

[52] U.S. Cl. ................... 424/249; 424/246; 424/248.5; 424/248.51; 424/248.53; 424/248.54; 424/248.56; 424/248.57; 544/211; 544/212

[58] Field of Search ............ 424/249, 246, 248.5, 424/248.51, 248.53, 248.54, 248.56, 248.57; 544/211, 212

[56] References Cited

U.S. PATENT DOCUMENTS 4,068,081  1/1978  Kay ........................ 424/249

*Primary Examiner*—Sam Rosen
*Attorney, Agent, or Firm*—Ernest G. Szoke

[57] ABSTRACT

New compositions containing as the principle active ingredient a 1,4-disubstituted-1,2-dihydro-1,3,5-triazin-2-one are used for remedial or prophylactic treatment of diarrhea and organic gastrointestinal disorders accompanied by diarrheal symptoms.

16 Claims, No Drawings

TRIAZINONES FOR VETERINARY USE

BACKGROUND

Diarrhea can result from a variety of physiological disorders including bacterial and parasitic infections, disease or debilitation of organs such as liver, adrenal and others. It can also occur as a result of other therapy or diet. In all cases, diarrhea is generally a symptom of organic gastrointestinal disorders and not itself a disorder. Chronic diarrhea is generally due to intestinal hypermotility and rapid transport. It may also be due to, or accompanied by hypersecretion of acid gastric juices or decreased reabsorption and may, in some instances, particularly those accompanied by hypersecretion, be associated with emotional tension and psychological conflicts. Therapeutic compositions administered in accordance with the present invention relieve diarrheal symptoms. Antidiarrheal compounds are, of course, well-known in the medicinal arts and take various forms. In particular there are a variety of products known which act systemically to provide antidiarrheal effects when administered in a manner which will enable the drug to be taken into the system at effective therapeutic levels. For example, U.S. Pat. No. 4,060,635 discloses a class of amidinourea derivatives with systemic antidiarrheal effects. Generally, however, compounds such as the amidinoureas exhibit their antidiarrheal properties only at dose levels which produce other significant side effects. The amidinoureas for example are also known to exhibit local anesthetic and antiarrhythmic effects as disclosed in a copending application by J. Diamond and G. Douglas, Ser. No. 671,762. It has recently been found that when such amidinoureas are treated with a derivatizing agent there is produced a cyclic derivative which has been characterized as a substituted 1,2-dihydro-1,3,5-triazin-2-one. It has now been found that when the cyclic derivatives are administered to animals in accordance with test protocols that have been established to mimic gastrointestinal disorders these compounds produce effects which can be correlated to therapeutically useful effects in the treatment of human patients for diarrhea and related gastrointestinal disorders. These compounds have been found to have a regulating effect on such disorders when produced in experimental models. In general, systemic antidiarrheal products have a therapeutic index such that effective antidiarrheal doses cannot be attained without significant side effects. It is an object of the present invention to provide a systemic antidiarrheal composition which can be administered at dosage levels that significantly inhibit or suppress the symptoms of diarrhea without other significant pharmacologic effects.

SUMMARY OF THE INVENTION

This invention pertains to novel therapeutic compositions and their use for treatment of conditions accompanied by diarrhea resulting in the suppression or alleviation of the symptoms of diarrhea. Therapeutic compositions for use in the treatment of patients suffereing diarrhea symptoms, are formulated with an effective amount of 1,4-disubstituted-1,2-dihydro-1,3,5-triazin-2-one combined with pharmaceutically acceptable excipients and provided in dosage forms suitable for oral administration whereby an effective amount is absorbed and transported to the site of action within the cells of the stomach and intestines.

DETAILED DESCRIPTION OF THE INVENTION

The 1,4-disubstituted-1,2-dihydro-1,3,5-triazin-2-ones which are used in the antidiarrheal treatments of this invention and which comprise a principal active ingredient in the antidiarrheal compositions of the invention are the compounds of the formula

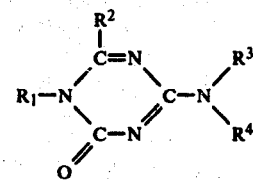

Formula I wherein $R_1$ is phenyl, benzyl or phenethyl; or phenyl, benzyl or phenethyl in which one or more of the phenyl hydrogens are substituted by lower alkyl, lower alkoxy, halo, halo-lower alkyl, amino, nitro, acyloxy, acylamino, hydroxy, cyano, carboxyl or lower alkyl sulfonyl, pyridyl or substituted pyridyl; $R_2$ is hydrogen or lower alkyl, and $R_3$ and $R_4$ are each independently selected from the group consisting of hydrogen, hydroxyl, lower alkanoyl, lower alkyl, lower alkenyl, lower alkynyl, lower alkoxy, halo lower alkyl, hydroxy lower alkyl, lower alkoxy lower alkyl, phenoxy lower alkyl, di-lower alkylamino lower alkyl or $R_3$ and $R_4$ together with the nitrogen to which they are attached form a 5 or 6 membered nitrogen heterocycle containing 0 to 1 additional hetero atoms which may be nitrogen, oxygen or sulfur; and their non-toxic salts.

As used herein, the term "lower alkyl" means a saturated or branched chain hydrocarbon containing from 1 to 6 carbon atoms such as methyl, ethyl, propyl, isopropyl, butyl, secondary butyl, tertiary butyl, isopentyl and the like. The term "substituted phenyl" is intended to include phenyl groups in which one or more of the hydrogen atoms has been replaced by a lower alkyl, hydroxy, nitro, amino, halo-lower alkyl, acyl, acylamino, lower alkoxy, cyano or lower alkyl sulphonyl. The term "substituted pyridyl" means a pyridyl group having one or more hydrogens replaced by lower alkyl, hydroxyl, nitro, amino, halo-lower alkyl, acyloxy, acylamino, lower alkoxy, cyano, carboxyl, or lower alkyl sulfonyl as in the case of substituted phenyl as defined above.

The term "halo" is intended to include all four halogens; i.e., chloro, bromo, iodo and fluoro, with chloro and fluoro being particularly preferred. The term "acyl" as used herein means an organic acid radical such as carboxyl, acetoxy, propionoxy, etc.

A particularly preferred group of 1,4-disubstituted-1,2-dihydro-1,3,5-triazin-2-ones useful in this invention are the compounds of the formula

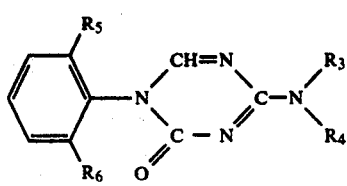

Formula II

Wherein $R_3$ and $R_4$ are independently selected from the group consisting of hydrogen, lower alkyl, hydroxyl, or lower alkoxy and $R_5$ and $R_6$ are each independently selected from the group consisting of hydrogen, halo, lower alkyl, lower alkoxy or halo lower alkyl; and the non-toxic salts thereof.

A still more preferred group are the compounds of formula II above wherein $R_3$ is hydrogen; $R_4$ is lower alkyl or lower alkoxy; and $R_5$ and $R_6$ are the same and are each lower alkyl or lower alkoxy.

The preparations of these compounds are described in an application filed simultaneously herewith and assigned to applicants' assignee. Said copending application is entitled "Triazinones" and the applicants are Douglas, Studt, Won and Dodson Ser. No. 959,611, filed Nov. 13, 1978. For a more complete description of the triazine derivatives, their synthesis and properties, reference may be had to such copending application the disclosure of which is incorporated herein by reference.

Pharmacological tests in animals which are generally recognized as models for determining antidiarrheal activity in humans, have shown that the compounds of the above structure when administered orally provide useful antidiarrheal effects at dose levels which are well tolerated and for which no significant side effects have been observed. Particularly, these compounds produce antidiarrheal effects without affecting the cardiovascular system or the central nervous system. Compounds which are effective in relieving diarrhea without any central nervous system, cardiovascular or local anesthetic effects are not generally available. Accordingly, the above compounds when formulated into therapeutic dosage forms provide a beneficial means for the treatment of gastrointestinal disorders accompanied by diarrhea.

The compositions of the present invention can be prepared in forms suitable for administration to animals by compounding an effective single dose amount of a compound of formula I above with known ingredients generally employed in the preparation of therapeutic compositions provided as tablets, capsules, lozenges, chewable lozenges, pills, powder, granules, suspensions, oil-in-water or water-in-oil emulsions, or other similar forms which can be taken orally. Since the compounds are readily absorbed into the blood stream from the stomach and intestines when taken orally, the preferred method of treatment is to give the drug orally which is also the safest and most practical route of administration. Optional methods can be used. Where, for example, the patient cannot swallow or has difficulty in swallowing, other methods of administration which permit the drug to be absorbed from the gastrointestinal tract or which deliver a solution of the drug directly to the blood stream can be employed.

In general, compounds of formula I above are indicated for use as pharmacotherapeutic agents in a wide variety of mammalian conditions which require relief of diarrhea symptoms accompanying abnormal action of the gastrointestinal system.

The dosage regimens in carrying out the pharmacotherapeutic methods utilizing the triazine compositions of this invention are those which insure maximum therapeutic response until improvement is obtained and thereafter the minimum effective level which gives relief. Thus, in general, the dosages are those that are therapeutically effective in the treatment of diarrhea. In general, the single oral dose will contain between about 1 mg and 100 mg (preferably in the range of 10 to 50 mg). Fractional or multiple doses can of course be given bearing in mind that in selecting the appropriate dosage in any specific case, consideration must be given to the patient's weight, general health, age, and other factors which may influence response to the drug. The drug response on oral administration usually follows within 10 to 30 minutes after administration and is maintained for 1 to 4 hours. The drug is generally given in single doses 2 to 4 times daily or as required to maintain an effective drug level in the blood stream for continuous relief of diarrhea symptoms.

Compositions intended for oral use may be prepared according to methods known generally in the art, such compositions may contain one or more agents selected from the group consisting of sweetening agents, flavoring agents, coloring agents and preserving agents, in order to provide a pharmaceutically elegant and palatable preparation. Orally, they may be administered in tablets, lozenges, aqueous or oily suspensions, dispersible powders or granules, emulsions, hard or soft capsules, or syrups or elixers which contain the active triazine ingredient in admixture with non-toxic pharmaceutically acceptable excipients. Excipients which may be, for example, inert diluents, such as calcium carbonate, sodium carbonate, lactose, calcium phosphate or sodium phosphate; granulating and disintegrating agents, for example, maize starch or alginic acid; binding agents, for example, starch, gelatin or acacia; and lubricating agents, for example, magnesium stearate, stearic acid or talc. The tablets may be uncoated or they may be coated by known techniques to make them more effective for example to delay disintegration or absorption or to make them more palatable or for other reasons for which orally administered drugs have been previously provided in coated form.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with an oil medium, for example, arachis oil, liquid paraffin or olive oil.

Aqueous solutions containing the active triazine form a further embodiment of this invention. Excipients suitable for aqueous suspensions, may be employed if desired. These excipients are suspending agents, for example, sodium carboxymethyl-cellulose, methyl-cellulose, hydroxypropyl-methylcellulose, sodium alginate, polyvinylpyrrolidine, gum tragacanth and gum acacia; dispersing or wetting agents may be a naturally occurring phosphatide, for example, lecithin; or condensation products or an alkylene oxide with fatty acids, for example, polyoxyethylene stearate; or condensation products of ethylene oxide with long-chain aliphatic alcohols, for example, heptadecaethyleneoxy-cetanol; or condensation products of ethylene oxide with partial esters derived from fatty acids and a hexitol, for example, polyoxyethylene sorbitol mono-oleate; or condensation products of ethylene oxide with partial esters derived from fatty acids and hexitol anhydrides, for example, polyoxyethylene sorbitan monoleate. The said aqueous suspensions may also contain one or more preservatives, for example, ethyl, or n-propyl, p-hydroxy benzoate, one or more coloring agents, one or more flavoring agents, and one or more sweetening agents, such as sucrose.

Oily suspensions may be formulated by suspending the active ingredient in a vegetable oil, for example, arachis oil, olive oil, sesame oil or coconut oil, or in a mineral oil, such as liquid paraffin. The oily suspensions may contain a thickening agent, for example, beeswax, hard paraffin or cetyl alcohol. Sweetening agents, such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending or wetting agents and suspending agents are exemplified by those already mentioned above. Additional excipients, for example, sweetening, flavoring and coloring agents, may also be present.

The compounds of this invention may also be in the form of oil-in-water emulsions. The oily phase may be a vegetable oil, for example, olive oil or arachis oils, or a mineral oil, for example, liquid paraffin or mixtures of these. Suitable emulsifying agents may be naturally-occurring gums, for example, gum acacia or gum tragacanth, naturally-occurring phosphatides, for example, soya bean lecithin, and esters or partial esters derived from fatty acids and hexitol anhydrides, for example, sorbitan mono-oleate. The emulsions may also contain sweetening and flavoring agents.

Syrups and elixirs may be formulated with sweetening agents, for example, glycerol, sorbitol or sucrose. Such formulations may also contain a demulcent, a preservative and flavoring and coloring agents. The pharmaceutical compositions may be in the form of a sterile injectionable preparation, for example, as a sterile injectable aqueous suspension. This suspension may be formulated according to the known art using those suitable dispersing or wetting agents and suspending agents which have been mentioned above. The sterile injectable preparation may also be a sterile injectable solution or suspension in a nontoxic parenterally-acceptable diluent or solvent, for example, as an aqueous solution buffered to a pH of 4.0 to 7.0 and made isotonic with sodium chloride.

Further, the active triazine may be administered alone or in admixture with other agents having the same or different pharmacological properties.

Generally, these compounds may be tableted or otherwise formulated for oral use so that for every 100 parts by weight of the composition, there are present between 5 and 95 parts by weight of the active ingredient.

The 1,4-disubstituted-1,2-dihydro-1,3,5-triazin-2-ones of Formula I and their pharmaceutically acceptable salts are also useful as veterinary medicines. In particular, these compounds are useful in preventing or treating diseases in food-producing animals especially diseases such as scours which is characterized by diarrheal symptoms. The compounds are useful in the treatment of neo-natal diarrhea in animals, particularly lambs, calves, and baby pigs. Scours in calves, lambs, baby pigs and foals can be prevented or improved by administering an effective amount of a compound of Formula I preferably as a food additive though other forms of administration can be used. The anti-scour treatment can be administered in combination with antibiotics such as neomycin or with other antibacterial or antiviral agents. The compounds of Formula I can also be used in the treatment of ruminants affected with bovine virus diarrhea or as a preventive measure. The compounds of Formula I are also useful in treating diarrhea in household pets, particularly cats and dogs, and can be administered prophylactically to prevent diarrhea or to relieve the diarrhea symptoms.

For the treatment of scours, the compounds of Formula I, and particularly the compounds of Formula II, and more specifically, those compounds exemplified in Examples 1 to 16 and 24 and 25 herein are administered orally to the infant animals for example with a plunger applicator bottle at doses in the order of 0.1 to 10 mg; preferably about 1 to 5 mg. administered daily. Higher doses can be used when tolerated especially in the case of larger animals. In general, a dose of about 10 mg. per day is effective in relieving symptoms of scours in calves, piglets, lambs and foals. The treatments are preferably administered prophylactically or within about 10 hours (preferably within about 5 hours) after onset of scours.

Various tests carried out in animal models show that the triazinones of formula I above exhibit reactions that can be correlated with antidiarrheal activity in humans. The following tests show the ability of these compounds to inhibit induced diarrhea in test animals indicative of antidiarrheal activity in humans. These are considered to be standard tests used to determine antidiarrheal properties. This correlation can be shown by the activities of compounds known to be clinically active and particularly previous experience in animals and humans with corresponding amidinoureas.

The test compound is dissolved in distilled water, unless otherwise stated.

1. Antagonism of Castor Oil-induced Diarrhea in Mice

A modified test described by Niemegeers et al. (Arzneim-Forscth 22, 516–518, 1972) was used. Groups of ten male Swiss Webster mice (22–25 g) were randomly selected for dosing. Castor oil (Fischer Scientific Co.), 0.3 ml/mouse, was given orally one hour after an oral dose of test compound or the vehicle. After dosing with castor oil, each mouse was placed into an individual wire cage and observed for six hours for diarrhea.

2. Antagonism of Castor Oil-induced Diarrhea in Rats

A test described by Niemegeers et al. (supra) was used. Groups of ten female Wistar rats (180–200 g) were randomly selected for dosing. In addition, groups of ten female Sprague-Dawly rats (180–200 g) were used to determine strain difference. Castor oil (Fisher Scientific Co.), 1 ml/rat was given orally one hour after an oral dose of test compound or the vehicle. After dosing with castor oil, each rat was placed into an individual wire cage and observed for six hours for diarrhea.

3. Antagonism of Chemically-induced Diarrhea in Mice

Male Swiss Webster mice (18–22 g) in groups of 10–20 mice were randomly selected for oral dosing with test compound or the vehicle one hour before the intraperitoneal injection of either 400 µg/kg of Carbachal (carbamycholine chloride, Sigma Chemical Co., St. Louis, Missouri); or, 200 µg/kg of serotonin creatinine sulfate (Schwartz/Mann Biochemicals, Orangeburg, N.Y.). After each mouse was injected, it was placed into an individual wire cage and observed for diarrhea.

4. Inhibition of the Gastrointestinal Transit Time of a Charcoal Meal in Mice

A charcoal suspension (10 ml/kg of a 10% suspension) was given orally to groups of ten Swiss Webster male mice (18–22 g) one hour after an oral dose of test compound or vehicle. The mice were sacrificed by cervical dislocation 30 minutes after the charcoal meal and the distance in millimeters that the charcoal meal traveled through the small intestine was measured and compared to the controls.

$$\frac{\text{Mean distance in controls} - \text{mean distance in treated}}{\text{Mean distance in controls}} \times$$

$$100 = \% \text{ Inhibiting}$$

5. The Effect of Naloxone on the Inhibitory Actions of Triazinone on Gastrointestinal Motility Male Swiss Webster mice (18–20 g) in groups of ten were randomly selected for dosing with test compound or the vehicle alone and concomitantly with naloxone. The naloxone was dissolved in saline.

The mice were given a charcoal meal (10 ml/kg of a 10% suspension) one hour after an oral dose of the vehicle or a test compound(s). Thirty minutes after the charcoal meal the mice were sacrificed by cervical dislocation and the distance in millimeters that the charcoal meal traveled through the small intestine was measured and compared to the controls.

6. Fecal Output Tolerance Study in Rats

Male Wistar rats (140–180 g) were given oral doses of either test compound, diphenoxylate HCl (suspended in methylcellulose or the vehicle (distilled water or methyl-cellulose) once a day for five consecutive days. Vehicle or the test compound were given daily 30 minutes before fecal collection. The feces were collected in a completely automated four-tiered metabolic cage over a 12-hour period consisting of three, four-hour intervals. Following collection, the feces were dried for four hours at 200° C. and weighed.

7. Prostaglandin Test

An intraperitoneal injection of 100 micrograms per kilogram of $PGE_2$ causes diarrhea in mice within ten minutes. Groups of mice were orally dosed with test compound at various dose levels after which the $PGE_2$ is given and ten minutes later the mice are checked for diarrhea to determine the $ED_{50}$.

Representative compounds of Formula 1 when subjected to testing in accordance with the above methods showed antidiarrheal activity comparable to that of the corresponding amidinoureas.

The results with a representative triazinone [1-(2',6'-dimethylphenyl) 4-methylamino-1,2-dihydro-1,3,5-triazin-2-one hydrochloride] are as follows.

1. Antagonism of Castor Oil-induced Diarrhea in Mice

An oral dose of 0.3 mls of castor oil caused diarrhea in 20 control mice within three hours. Test compound, given to ten mice per dose level one hour before an oral dose of castor oil, protected the mice from diarrhea in a dose-related way over a period of six hours.

2. Antagonism of Castor Oil-induced Diarrhea in Rats 1-(2',6'-dimethylphenyl)-4-methylamino-1,2-dihydro-1,3,5-triazin-2-one hydrochloride protected Wistar and Sprague-Dawley female rats from diarrhea at a potency ratio comparable to that of diphenoxylate and loperamide with better duration of action.

3. Antagonism of Chemically-induced Diarrhea

Serotonin injected intraperitoneally at 200 μg/kg caused diarrhea in 15 control mice within 15 minutes after its injection. 1-(2',6'-dimethylphenyl)-4-methylamino-1,2-dihydro-1,3,5-triazin-2-one hydrochloride given orally to ten mice per dose level protected the mice from serotonin-induced diarrhea.

An intraperitoneal injection of 400 μg/kg of carbachol caused diarrhea in 15 control mice within 20 minutes after its injection. 1-(2',6'-dimethylphenyl)-4-methylamino-1,2-dihydro-1,3,5-triazin-2-one hydrochloride given orally to five or ten mice per dose level protected the mice from carbachol-induced diarrhea.

4. Inhibition of the Gastrointestinal Transit Time of a Charcoal Meal in Mice

Twenty mice were used as controls and ten mice at each dose level. Inhibition with 1-(2',6'-dimethylphenyl)-4-methylamino-1,2-dihydro-1,3,5-triazin-2-one hydrochloride was dose-related.

5. The Effect of Naloxone on the Inhibitory Actions of 1-(2',6'-dimethylphenyl)-4-methylamino-1,2-dihydro-1,3,5-triazin-2-one hydrochloride Naloxone is a well-known specific antagonist of morphine-like compounds. As previously reported, diphenoxylate was antagonized by naloxone competitively in the charcoal meal test. Naloxone had no effect on the actions of 1-(2',6'-dimethylphenyl)-4-methylamino-1,2-dihydro-1,3,5-triazin-2-one hydrochloride. The dose of naloxone used in this test did not, by itself, change the gastrointestinal transit time of a charcoal meal.

6. Fecal Output Tolerance Study in Rats

Groups of rats, five in each group, were given 1-(2',6'-dimethylphenyl)-4-methylamino-1,2-dihydro-1,3,5-triazin-2-one hydrochloride and diphenoxylate, for five consecutive days. The triazinone showed no tolerance over the five day period, while diphenoxylate caused a decrease in activity starting on day 2 and continuing through day 5. After five days, diphenoxylate had lost 72% of its original activity seen on day 1.

7. Antagonism of Prostaglandin $E_2$ ($PGE_2$)-induced Diarrhea in Mice

An intraperitoneal injection of 100 μg/kg $PGE_3$ (Analabs Inc., North Haven, Conn.) caused diarrhea in 15 control mice within 15 minutes after its injection. 1-(2,6-dimethylphenyl)-4-methylamino-1,2-dihydro-1,3,5-triazin-2-one hydrochloride given orally to ten mice per dose level protected the mice from $PGE_3$-induced diarrhea in a dose-related way.

Unlike the amidinoureas which generally have local anesthetic properties, the 1,4-disubstituted-1,2-dihydro-1,3,5-triazin-2-ones of formula I have been found to be more specific, and surprisingly, effective antidiarrheal doses show little or no classical local anesthetic effects nor do they show any significant cardiovascular effects. Such compounds are particularly useful as antidiarrheal agents where it is desirable to achieve an antidiarrheal effect with a minimum of side effects and these compounds are therefore especially suited to the treatment of gastrogenic diarrhea.

The tests employed to determine the separation of local anesthetic and cardiovascular activity at effective antidiarrheal doses with representative compounds of formula I above are as follows:

Several different procedures generally employed in testing for local anesthetic activity are used to determine local anesthetic effects. These tests have been used extensively in the past and have given satisfactory results in defining the local anesthetic properties of compounds.

A discussion of experimental methods for evaluating local anesthetic properties of drugs is found in *Evaluation of Drug Activities: Pharmacometrics*, Vol. 1, Ed by D. R. Lawrence and A. L. Bacharach, Academic Press, Inc. (London) Ltd. (1964). Applicants herewith incorporate by reference Chapter 9 of this book entitled "Local Anesthetics", pages 204–214.

Tests which show the lack of CNS and other side effects of the preferred antidiarrheal triazinones include the following.

1. Effect on Hexobarbital-induced Loss of Righting Reflex 1-(2',6'-dimethylphenyl)-4-methylamino-1,2-dihydro-1,3,5-triazin-2-one hydrochloride and a vehicle given orally 30 minutes before hexobarbital were compared for their effect on the duration of the loss of righting reflex (failure to right within five seconds) induced in groups of Swiss Webster mice (10/group, 18–20 g) by the intraperitoneal injection of hexobarbital (100 mg/kg, I.P.).

2. Effect on Plasma Glucose in Rats

Groups of 5–10 male Sprague-Dawley rats (170–210 g) were orally dosed with 1-(2,6-dimethylphenyl)-4-methylamino-1,2-dihydro-1,3,5-triazin-2-one hydrochloride or the vehicle. Three hours after dosing, the rats were sacrificed by decapitation and blood was collected for plasma glucose evaluation.

3. Effect on Inducing Emesis in Dogs

Female beagle dogs (6.0–10 kg) were randomly selected for intravenous dosing with 1-(2',6'-dimethylphenyl)-4-methylamino-1,2-dihydro-1,3,5-triazin-2-one hydrochloride. Each dose of the test compounds was given to either two or four dogs. Immediately after the injection, the dogs were observed for emesis for a period of up to one hour.

The results with a representative triazinone are as follows:

1. Effect on Hexobarbital-induced Loss of Righting Reflex 1-(2'6'-dimethylphenyl)-4-methylamino-1,2-dihydro-1,3,5-triazin-2-one hydrochloride in doses as large as four times the $ED_{100}$ dose in the castor oil test in mice, had no effect on the duration of hexobarbital-induced loss of righting reflex.

2. Effect on Plasma Glucose in Rats

Groups of rats, five per group, were given oral doses of 1-(2',6'-dimethylphenyl)-4-methylamino-1,2-dihydro-1,3,5-triazin-2-one hydrochloride. A dose-related elevation of plasma glucose resulted.

3. Effect on Inducing Emesis in Dogs

There is a marked difference between 1-(2',6'-dimethylphenyl)-4-methylamino-1,2-dihydro-1,3,5-triazin-2-one hydrochloride and the corresponding amidinourea in causing emesis in beagle dogs. 1-(2',6'-dimethylphenyl)-4-methylamino-1,2-dihydro-1,3,5-triazin-2-one hydrochloride caused no emesis at a dose as much as 10 times the dose at which the corresponding amidinourea produced emesis in three of four dogs within a three minute period.

Various tests and the results intended to illustrate the effects of the triazinones on the cardiovascular system are given below.

Cardiovascular Activity of 1-(2',6'-dimethylphenyl)-4-methylamino-1,2-dihydro-1,3,5-triazin-2-one hydrochloride Intravenous doses greater than effective antidiarrheal amounts of 1-(2',6'-dimethylphenyl)-4-methylamino-1,2-dihydro-1,3,5-triazin-2-one hydrochloride did not significantly change arterial blood pressure, but produced moderate reductions in heart rate. Sympathetically-mediated cardiovascular reflex activity was only slightly reduced. Blood pressure responses to challenge doses of autonomic antagonists were not significantly changed.

Antiarrhythmic Effects in Ouabain-intoxicated Dogs

Following ouabain intoxication, one dog received an I.V. infusion of 1-(2',6'-dimethylphenyl)-4-methylamino-1,2-dihydro-1,3,5-triazin-2-one hydrochloride. After a total dose of more than twice the effective antidarrheal dose (orally) the heart rate was slightly reduced and the blood pressure elevated in association with partial conversion from ectopic ventricular tachycardia to a primarily nodal rhythm. A second dog received an I.V. infusion at two times the rate of the first for total dose twice as large. In this dog, heart rate was slightly reduced and blood pressure was elevated following the infusion, but there was no conversion from the ouabain-induced ventricular ecotopic rhythm. In previous studies, ouabain-intoxicated dogs receiving the corresponding amidinourea at the lower dose level consistently converted to normal sinum rhythm after a total dose less than one fourth the amount of triazinone.

Local Anesthetic Effects in Guinea Pigs

Intradermal injections of 1-(2',6'-dimethylphenyl)-4-methylamino-1,2-dihydro-1,3,5-triazin-2-one hydrochloride were essentially ineffective in protecting against dermal pain responses at levels that produce antidiarrheal action. Higher concentrations showed some effect.

Three different procedures generally employed in testing for local anesthetic activity have been used to determine the local anesthetic properties of the compounds of this invention. These tests have been used extensively in the past and have been proven to provide satisfactory results in establishing local anesthetic properties of compounds and provide sufficient results to enable one to use the same.

A discussion of these experimental methods which would enable the skilled artisan to carry out this invention in the manner he sees fit will be found in *Evaluation of Drug Activities: Pharmacometrics*, Vol. 1, Ed by D. R. Lawrence and A. L. Bacharach, Academic Press, Inc. (London) Ltd. (1964). Applicants herewith incorporate by reference Chapter 9 of this book entitled, "Local Anesthetics", pages 205–214.

An additional test method used to examine the unique local anesthetic activity of the novel triazine compounds of this invention involves direct application to the isolated desheathed sciatic-peroneal-tibial trunk of the bullfrog. The methodology used is as follows:

All drug solutions were applied to 15 mm segments of desheathed trunks situated between stimulating and recording electrodes employing a standard pharmacologic technique for observing the conduction blocking effects of local anesthetics.

Briefly summarized, the technique allows nerve impulses to be initiated by means of an electrical stimulus applied to a drug-free segment of a trunk and to be conducted through the treated segment. Recording electrodes placed on the distal side of the treated segment detect only those impulses that were conducted through the 15 mm segment. By relating the amplitude of the recorded compound spike potential to that recorded before the application of drug treatment, an index is available for the proportion of fibers that could conduct impulses through 15 mm of treated length. This index is referred to as "percent of control spike height" or "percent reduction of Spike height" or "percent block of conduction".

The source of the nerves is the bullfrog, Rana castesbeiana. During dissection, the nerves are exposed to Ringer solution having the following composition: 110 mM NaCl, 3.0 mM KCl, 1.8 mM $CaCl_2$, 20 mM $NaHCO_3$, 2 mM phosphate buffer. The solution is bubbled with 95% $O_2$, 5% $CO_2$ to maintain a pH of 7.2±0.05 at room temperature (22°-24° C.).

Preparation of Ringer solution with test substance:

First, a quantity of drug is weighed out which would make a 50 mM solution when dissolved in 5.0 ml of Ringer. The drug is dissolved in 0.4 ml of absolute ethanol by stirring for 10 minutes at high speed on a Genie Vortex apparatus. The solution is then brought to 5.0 ml with standard Ringer solution. This results in a 50 mM solution of drug in Ringer solution. The drug solution is then diluted 10 times with Ringer solution to give a final concentration of 5.0 mM. The final solution is bubbled with 95% $O_2$, 5% $CO_2$ to give a pH of 7.2. The final concentration of ethanol is 0.172 M.

To control for the ethanol in the drug solution, the drug-free Ringer solution used to recover nerves from drug effect was made with the same final concentration of ethanol. This ethanol had no effect on conduction.

The same general procedure was used to prepare a solution of the test drug in a dimethylsulfoxide Ringer solution. The final concentration of dimethylsulfoxide (DMSO) was 0.101 M. DMSO had no effect on conduction.

Representative compounds of Formula I when tested by this method showed the following results.

1-(2',6'-dimethylphenyl)-4-methylamino-1,2-dihydro-1,3,5-triazin-2-one proved to have essentially no conduction blocking action at a concentration of 5 1 mM, which is the high end of concentrations used on desheathed frog trunks with bonafide local anesthetic agents. In 4 separate experiments, the average reduction in the A B spike potential was only 10%±1.6 (S.E.M.) after 30 minutes contact with the drug. This feeble effect is contrasted with that of 5 mM the known amidino urea (1142, which caused a mean reduction of 77%±8.3 (N=3) within 10 minutes of contact; and a total block within 20 minutes in 2 of 3 trunks.

The following examples are given by way of illustrating the preparation of the active triazinones used in the method and compositions of this invention. Novel therapeutic compositions are also exemplified. It will be understood that variations in amounts and adjuvants used in compounding suitable compositions can be made without departing from the teaching of this invention which is the administration of a 1,4-disubstituted-1,2-dihydro-1,3,5-triazin-2-one of formula I in a manner and in amounts sufficient to provide and maintain an antidiarrheally effective level in the G.I. tract for either prophylactic or therapeutic use. If desired, the compounds can be formulated with other active ingredients or administered with other drugs or as part of a program of therapy that includes suppression of diarrhea. The salts of compounds of formula I, including acid addition salts and quarternary ammonium salts are particularly suitable for preparing pharmaceutical compositions. The acid addition salts of strong acids such as the hydrochloride, the hydrobromide, sulfate, nitrate, phosphate, methane sulfonate, benzene sulfonate and the like are especially useful. The salts of any strong Lewes acids can be used.

EXAMPLE 1

Preparation of 1-(2',6'-dimethylphenyl)-4-methylamino-1,2-dihydro-1,3,5-triazin-2-one About 200 mg of 1-(2,6-dimethylphenyl)-3-methylamidinourea hydrochloride was introduced in a gas chromatograph hypo vial and dissolved in 1 ml of acetonitrile. To the solution was added 0.2 ml of DMF DMA reagent. The vial was sealed with crimper and heated at 105° C. for 15 minutes in an oven. Seven vials were made. The contents of the vials were then put into a long-neck round bottom flask and evaporated to dryness by a flask evaporator. The solid mass was dissolved in a mixture of 30 ml of $CHCl_3$ and 20 ml of water and shaken vigorously in a 60 ml separatory funnel. The aqueous layer was discarded and 20 ml of water was added and shaken. The $CHCl_3$ layer was then taken and about 10 g of anhydrous $Na_2SO_4$ was added, the $CHCl_3$ solution was decanted into a flask and evaporated to dryness. The solid material was dissolved in 2-pentanone (about 80 ml) at 70° C. The solution was concentrated and crystallized upon cooling. The crystals were collected and dried in a desiccator with $P_2O_5$ with vacuum for one hour.

| Elemental Analysis MW: 230.26 MP: 225°-226° C. | | | |
|---|---|---|---|
| | C | H | N |
| Calculated | 62.59 | 6.13 | 24.33 |
| Found | 62.84 | 6.15 | 24.28 |

EXAMPLE 2

Preparation of 1-(2',6'-diethylphenyl)-4-methylamino-1,2-dihydro-1,3,5-triazin-2-one The same procedure was followed as in Example 1 above using 1-(2,6-diethylphenyl)-3-methylamidinourea as the starting material and using as the recrystallization medium a mixed solvent of pentanone and hexane (30:10).

| Elemental Analysis MP: 210°-211° C. | | | |
|---|---|---|---|
| | C | H | N |
| Calculated | 65.09 | 7.02 | 21.89 |
| Found | 65.34 | 7.01 | 21.83 |

EXAMPLE 3

1-(2',6'-dimethylphenyl)-4-methylamino-1,2-dihydro-1,3,5-triazin-2-one-hydrochloride To a suspension of 10.0 g (30.0 m mole) of 1-(2,6-dimethylphenyl)-3-methylamidinourea hydrochloride in acetonitrile ($CH_3CN$) (50 ml) was added 9.3 g (78.0 m mol) of dimethylformamide dimethylacetal (DMF-DMA) and the resulting solution in a bomb was heated to 100°–105° C. for one hour. After cooling, the reaction mixture was placed in a round bottom flask and concentrated under reduced pressure. The residue was partitioned between $H_2O$ and $CHCL_3$ and the layers separated. The aqueous layer was extracted with $CHCl_3$ (1×50 ml). The combined $CHCl_3$ extracts were washed with $H_2O$ (1×50 ml) dried ($MgSO_4$) and concentrated under reduced pressure. A small amount of the residue was triturated in hexanes to give a white solid, having melting point 224 OC NMR and IR showed the product to be identical with that of Example 3. The remainder of the residue was dissolved in MeOH and acidified with HCl/MeOH. The MeOH was removed under vacuum and the residue crystallized from $CH_3CN$ to give 6.8 g (65%) of 1-(2,6-dimethylphenyl)-4-methylaminotriazin-2(6H)-one hydrochloride, melting point 234°–8° C. (decomposition).

| Analysis calculated for: $C_{12}H_{15}ClN_4O$ | | | |
|---|---|---|---|
| C | H | N | Cl |
| Calculated: 54.04 | 5.67 | 21.01 | 13.29 |
| Found: 54.14 | 5.80 | 21.90 | 13.28 |

EXAMPLE 4

1-(2',6'-dimethylphenyl)-4-methylamino-1,2-dihydro-1,3,5-triazin-2-one methanesulfonate A solution of 6.0 g (0.026 moles) of 1-(2,6-dimethylphenyl)-4-methylamino-dihydro-1,3,5-triazin-2-one in 100 ml iPA was prepared with warming. To the warm solution was added 2.0 ml (0.031 moles) of methane-sulfonic acid. The mixture became hot and crystals of white crystalline solid began to form almost immediately. The mixture allowed to cool to room temperature in tap water and filtered. The solution was washed with IPA/$Et_2O$ to give 8.00 g of product which was dried overnight at 50°–60° C. in a vacuum. Obtained 8.0 g of 1-(2,6-dimethylphenyl)-4-methylaminodihydro-1,3,5-triazin-2-one methanesulfonate after drying.

| Calculated for: $C_{13}H_{18}N_4O_4S$ MW: 326.35 MP: 262°–65° C. dec. | | | |
|---|---|---|---|
| C | H | N | S |
| Calculated: 47.84 | 5.57 | 17.17 | 9.80 |
| Found 48.03 | 5.71 | 17.25 | 10.27 |

EXAMPLE 5

1-(2',6'-diethylphenyl)-4-methylamino-1,2-dihydro-1,3,5-triazin-2-one hydrochloride To a suspension of 22.8 g (80.0 mmol) of 1-(2,6-diethylphenyl)-3-methylamidinourea hydrochloride in $CH_3CN$ (100 ml) were added 19.1 g (160.0 mmol) of DMF-DMA and the reaction mixture was heated at reflux for 3 hours. The $CH_3CN$ was removed under reduced pressure and the residue partitioned between $CHCl_3$ and $H_2O$. The layers were separated and the aqueous layer extracted with $CHCl_3$ (1×100). The combined $CHCl_3$ extracts were washed with $H_2O$ (1×100 ml), dried ($MgSO_4$) and concentrated under reduced pressure to give an off-white solid, which by NMR confirmed the desired free base. The solution was dissolved in $H_2OH$ and acidified with HCl/MeOH and the MeOH removed under reduced pressure to give an off-white solid which was crystallized from $CH_3CN$ to give after vacuum drying the weekend (105° C., house vacuum) 16.7 g (71%) of crude product. The material was recrystallized from $CH_3CN$ (a hot filtration was necessary to remove some undissolved solid) to give 11.0 g (47%) of desired product as a white crystalline solid:

| Analysis calculated for: $C_{14}H_{18}N_4OHCl$ MP: 208°–15° C. | | | |
|---|---|---|---|
| C | H | N | Cl |
| Calculated: 57.04 | 6.50 | 19.01 | 12.03 |
| Found: 57.14 | 6.51 | 19.38 | 12.01 |

EXAMPLE 6

4-dimethylamino-1-(2',6'-dimethylphenyl)-1,2-dihydro-1,3,5-triazin-2-one hydrochloride To a suspension of 19.0 g (0.07 mole) of 1-(2,6-dimethylphenyl)-3-(N,N-dimethyl)-amidinourea in acrylonitrile (100 m) were added 16.7 g (0.14 mole) of DMF-DMA and the mixture refluxed for 2 hours. The acrylonitrile was removed under reduced pressure and the residue partitioned between $H_2O$ and $CHCl_3$. The layers were separated and the aqueous layer extracted with $CHCl_3$ (1×100 ml). The $CHCl_3$ extracts were washed with $H_2O$ (1×50 ml), dried over $MgSO_4$ and concentrated at reduced pressure to give an oil. Trituration of the oil in EtOH precipitated a white solid which was filtered and washed with EtOH to give the desired product after air drying. The solid was dissolved in MeOH and acidified with HCl/MeOH. The MeOH was removed under reduced pressure to give a white solid which was triturated with $CH_3CN$, filtered and washed with $CH_3CN$ to give 7.5 g (38%) of product which by NMR seemed to be a hydrate or wet. The solid was vacuum dried for 6 hours at 100° C. under vacuum.

| Analysis calculated for: $C_{13}H_{10}N_4O \cdot HCl$ | | | |
|---|---|---|---|
| C | H | N | Cl |
| Calculated: 55.61 | 6.10 | 19.96 | 12.63 |
| Found: 55.81 | 5.96 | 20.31 | 12.46 |

EXAMPLE 7

1-(2-chloro-6-methylphenyl)-4-methylamino-1,2-dihydro-1,3,5-triazin-2-one

To a suspension of 11.1 g (40 mmol) of 1-(2-chloro-6-methylphenyl)-3-methyl amidinourea hydrochloride in 45 ml of $CH_3CN$ was added 5.7 g (48 mmol) of dimethylformamide dimethylacetal which was washed into the flask with an additional 5 ml of $CH_3CN$.

The reaction mixture was stirred for 1.5 hours after which an aliquot of the reaction product which had been dissolved in MeOH showed there to be one major spot with $R_f$ equal to that of 1-(2-chloro-6-methylphenyl)-4-methylamino-1,2-dihydro-1,3,5-triazin-2-one and two minor spots of very small $R_f$, one at the origin and one of the same $R_f$ as the starting material amidinourea hydrochloride. The reaction mixture was allowed to stir an additional 0.5 hour and the solid was filtered to yield 1-(2-chloro-6-methylphenyl)-4-methylaminodihydro-1,3,5-triazin-2-one, (EtOAc:MeOH; 9:1). It has the same two impurities as the crude reaction mixture. 7.7 g of the crude mixture was recrystallized from absolute EtOH; melting point 257.5°–258.5° C.

Most of the 1-(2-chloro-6-methylphenyl)-4-methylaminodihydro-1,3,5-triazin-2-one (5.0 g, 65% was insoluble in hot absolute EtOH. The residue was filtered off to yield product having melting point 254°–255.5° C. The product was placed in the vacuum dissicator at 100° C. for 3 hours to yield 1-(2-chloro-6-methylphenyl)-4-methylaminodihydro-1,3,5-triazin-2-one, melting point 255.5°–257.5° C.; NMR still showed about 2% $CH_3CN$ impurity. 1-(2-chloro-6-methylphenyl)-4-methylaminodihydro-1,3,5-triazin-2-one was returned to the dissicator at 100° C. for overnight. 4.40 g of the product was dissolved in hot MeOH (100 ml) and EtOAc was added and the solution was concentrated on a hot plate until the solution became cloudy. The solution was allowed to cool to ambient temperature and then was placed in the refrigerator. The solid was filtered to yield 0.99 g, melting point 257.5°–258.5° C.

The filtrate produced a second crop of crystals after sitting overnight. This was filtered to yield an additional 1.41 g of product with melting point 258° C.

The crystalline products were combined and submitted for analysis as 1-(2-chloro-6-methylphenyl)-4-methylaminodihydro-1,3,5-triazin-2-one.

| Analysis calculated for: $C_{11}H_{11}ClN_4O$ | | | | |
|---|---|---|---|---|
| Calculated: | 52.70% | 4.42% | 22.35% | 14.14% |
| Found: | 52.61% | 4.48% | 22.69% | 13.89% |

EXAMPLE 8

1-(2',6'-dimethylphenyl)-4-n-butoxyamino-1,2-dihydro-1,3,5-triazin-2-one

To a magnetically stirred suspension of 12.06 g (38 mmol) of 1-N-butoxy-3-(2,6-dimethylphenyl) amidinourea hydrochloride in 25 ml of $CH_3CN$ was added 9.11 g (76 mmol) of N,N-dimethyl-formamide dimethyl acetal and another 25 ml of $CH_3CN$. All of the solid dissolved after the reaction was stirred for 5 minutes. The reaction solution was refluxed for two hours and allowed to come to ambient temperature, then concentrated in vacuo to yield the desired product as a white solid. This was combined with 200 ml of $H_2O$ to an insoluble, thin gummy solid which was transferred to a separatory funnel and extracted with $CHCl_3$ (3×75 ml). The organic layers were combined, washed with $H_2O$ (2×75 ml) and saturated aqueous brine (1×75 ml). All aqueous washes were combined and back-extracted with (2×50 ml), dried ($Mg_2SO_4$), filtered and concentrated in vacuo to yield 1-(2,6-dimethylphenyl)-4-n-butoxyamino-1,2-dihydro-1,3,5-triazin-2-one, as a white solid containing some liquid. Tlc (3% $NH_4OH$/iPA) shows four spots, one of same $R_f$ as starting material. The product was triturated with iPA to yield a white solid: m.p. 144°–145° C.

| Elemental analysis calculated for: $C_{15}H_{20}N_4O_2$ | | | |
|---|---|---|---|
| | C | H | N |
| Calculated: | 62.48% | 6.99% | 19.43% |
| Found: | 62.49% | 6.98% | 19.57% |

The filtrate was concentrated in vacuo to yield a yellow oil. This oil was triturated with about 20 ml iPA and a white solid crystallized out. The solid was filtered and washed with cold iPA to yield product with melting point 144°–145.5° C. which appeared to be identical to the product obtained above.

EXAMPLE 9

1-(2',6'-dimethylphenyl)-4-sec-butoxyamino-1,2-dihydro-1,3,5-triazin-2-one

To a magnetically stirred suspension of 15.6 g (49.5 mmol) of 1-(2,6-dimethylphenyl)-3-sec-butoxyamidinourea hydrochloride in 25 ml of $CH_3CN$ was added 11.8 g (99 mmol) of N,N-dimethylformamide dimethylacetal (Eastman #10292, Lot #B6X) and another 25 ml of $CH_3CN$. The solid dissolved at this point. The reaction solution was heated to reflux. After two hours the reaction solution was removed from the heat and allowed to cool to ambient temperature, transferred to a larger flask, and concentrated in vacuo.

The white solid residue was taken up in $CHCl_3$ and washed with $H_2O$ (3×50 ml). All aqueous layers were combined and back-extracted with $CHCl_3$ (2×50 ml). All organic layers were combined and washed with saturated aqueous brine (1×50 ml). The organic layer was separated, dried ($MgSO_4$), filtered and concentrated in vacuo to yield white solid oil (20.2 g); impurities from, and possible starting material are present. A small amount of product was dissolved in boiling $Et_2O$, diluted with hexane and concentrated until solid began to form. The solid which crystallized out was 1-(2,6-dimethylphenyl)-4-sec-butoxyamino-1,2-dihydro-1,3,5-triazin-2-one.

The entire amount of product was dissolved in boiling $Et_2O$, filtered, concentrated in a steam bath, and diluted with hexane until a white solid crystallized out. The solution was cooled to ambient temperature.

The product was filtered and washed with hexane to yield product with melting point 149° C.

| Analysis calculated for: $C_{15}H_{20}N_4O_2$ | | | |
|---|---|---|---|
| | C | H | N |
| Calculated: | 62.48% | 6.99% | 19.43% |
| Found: | 62.41% | 7.01% | 19.27% |

EXAMPLE 10

4-methylamino-1-phenyl-1,2-dihydro-1,3,5-triazin-2-one hydrochloride

To a suspension of 9.5. g (40.0 mmol) of 1-phenyl-3-methylamidinourea hydrochloride hemihydrate in $CH_3CN$ (50 ml), was added 9.5 g (80.0) of DMF-DMA and the mixture heated to 105°–110° C. in a closed bomb for two hours. The reaction mixture was allowed to cool. A solid precipitated. This was filtered and washed with $CH_3Cl$. The filterate was concentrated and the residue was diluted with $H_2O$. The precipitated solid was filtered, washed with $H_2O$ and $Et_2O$. The two fractions were combined and crystallized from $CH_3CN$.

4.5 g (56%) of white solid, which by NMR seems to be the hemihydrate, melting point 223°-4° C. was obtained.

| Analysis calculated for: $C_{10}H_{10}N_4O$ | | | |
|---|---|---|---|
| | C | H | N |
| Calculated: | 59.40% | 4.98% | 27.71% |
| Found: | 59.27% | 4.71% | 28.71% |

The solid was dissolved (warmed on steam bath) in MeOH and acidified with HCl/MeOH. The MeOH was removed under reduced pressure to give a white solid 4-methylamino-1-phenyltriazin-2(6h)-one hydrochloride which was crystallized from $CH_3OH/CH_3CN$.

EXAMPLE 11

1-(2-methylphenyl)-4-ethylamino-1,2-dihydro-1,3,5-triazine-2-one

To a magnetically stirred suspension of 9.02 g (35.2 mmol) of 1-(2-methylphenyl)-3-ethylamidinourea hydrochloride in 30 ml of $CH_3CN$, was added 8.40 g (70.5 mmol) of N,N-dimethylformamide dimethylacetal and 20 ml of $CH_3CN$. All of the solid dissolved. The reaction mixture was refluxed for two hours, allowed to come to ambient temperature, and partitioned between $CHCl_3$ and $H_2O$.

The layers were separated and the aqueous layer was extracted with $CHCl_3$ (1×50 ml). The organic layers were combined, washed with $H_2O$ (1×50 ml) and saturated brine (1×50 ml). These last two aqueous layers were combined and back-extracted with $CHCl_3$. All organic layers were combined, dried ($MgSO_4$), filtered and concentrated in vacuo to yield 1-(2-methylphenyl)-4-ethylaminodihydro-s-triazin-2-one as a white solid, 8.6 g. After recrystallizing from EtOAc, the product was filtered and dried on the buckner funnel under vacuum to give the desired end product with melting point 208.5°-209.5° C.

| Analysis calculated for: $C_{12}H_{14}N_4O$ | | | |
|---|---|---|---|
| | C | H | N |
| Calculated: | 62.59% | 6.13% | 24.33% |
| Found: | 62.39% | 5.96% | 24.64% |

EXAMPLE 12

1-(2',6'-dichlorophenyl)-4-methylamino-1,2-dihydro-1,3,5-triazin-2-one

To a magnetically stirred suspension of 11.88 g (40 mmol) of 1-(2,6-dichlorophenyl)-3-methylamidinourea hydrochloride in 30 ml of $CH_3CN$ was added 9.52 g (80 mmol) of N,N-dimethylformamide dimethylacetal in 20 ml of $CH_3CN$. The solid material began to dissolve immediately but in a few minutes, before the starting material had dissolved, another fine white solid began to precipitate out. The reaction mixture was stirred at ambient temperature for one hour then heated to reflux for two hours. After two hours, the reaction mixture was allowed to come to ambient temperature and the white solid precipitate filtered out to yield the desired product, melting point 270° C.; TLC (EtoAc 9:1); one major spot, one minor spot at origin. A small sample recrystallized from $CH_3OH/EtOAc$ gave one spot on TLC. (9.6 g, 89%) was crystallized from MeOH to yield 1-(2,6-dichlorophenyl)-4-methylaminodihydro-s-triazin-2-one.

The recrystallizing solution was concentrated from 1400 ml to 700 ml, then refrigerated after a lot of solid had come out. After refrigeration for several hours, the solid was filtered and washed with cold MeOH to yield additional product having melting point 270° C. TLC (EtOAc/MeOH; 9:1) still shows very small spot at origin.

| Analysis calculated for: $C_{10}H_8N_4Cl_2O$ | | | | |
|---|---|---|---|---|
| | C | H | N | Cl |
| Calculated: | 44.30% | 2.97% | 20.67% | 26.16% |
| Found: | 44.24% | 2.73% | 20.80% | 26.09% |

EXAMPLE 13

1-(2-methylphenyl)-4-methylamino-1,2-dihydro-1,3,5-triazin-2-one

To a magnetically stirred suspension of 9.72 g (40 mmol) of 1-(2-methylphenyl)-3-methylamidinourea hydrochloride in 30 ml of $CH_3CN$ was added 9.52 g (80 ml) of N,N-dimethylformamide dimethylacetal. After the mixture had been further diluted with 25 ml $CH_3CN$ and stirred for 5 minutes, all of the solid had dissolved. TLC(3% $NH_4OH/IPA$) showed a new spot; about equal in size to a spot in starting material; (EtOAc/MeOH; 9:1) shows mostly a new spot. The solution was refluxed for two hours. The reaction mixture was allowed to cool to ambient temperature. The reaction mixture was then poured into $CHCl_3/H_2O$ and separated. The aqueous layer was extracted with $CHCl_3$ (for a total of 3×50 ml). The organic layers were combined and washed with $H_2O$ (2×50 ml). The aqueous layers were combined and back-extracted with $CHCl_3$ (1×50 ml). All organic layers were combined, dried, filtered and concentrated in vacuo to yield the product which was recrystallized from absolute EtOH, filtered and washed with cold absolute EtOH and air-dried. The product was 1-(2-methylphenyl)-4-methylaminodihydro-1,3,5-triazin-2-one, melting point 191.5°-192.5° C.

| Analysis calculated for: $C_{11}H_{12}N_4O$ | | | |
|---|---|---|---|
| | C | H | N |
| Calculated: | 61.10% | 5.59% | 25.91% |
| Found: | 61.02% | 5.80% | 26.25% |

EXAMPLE 14

1-(2',6'-dimethylphenyl)-4-(2,2,2-trifluoroethylamino)-1,2-dihydro-1,3,5-triazin-2-one To a suspension of 130 g (40.0 mmol) of 1-(2,6-dimethylphenylcarbamoyl)-3-(2,2,2-trifluoroethyl) guanidine hydrochloride in $CH_3CN$ (50 ml) were added 95 g (80.0 mmol) of DMF-DMA and the mixture heated at reflux for two hours. The solvent was removed under vacuum, and the residue partitioned between $CHCl_3$ and $H_2O$. The layers were separated and the aqueous layer was extracted with $CHCl_3$ (1×100 ml). The extracts were dried ($MgSO_4$) and concentrated to give a white solid which was crystallized from absolute EtOH to give after heating under vacuum at 100° C. for one hour; 9.5 g (80%) of 1-(2,6-dimethylphenyl)-4-(2,2,2-trifluoroethylamino)dihydro-1,3,5-triazin-2-one; melting point 212°-3° C.

| Analysis calculated for: $C_{13}H_{13}F_3N_4O$ | | | |
|---|---|---|---|
| | C | H | N | F |
| Calculated: | 52.35% | 4.39% | 18.78% | 19.11% |
| Found: | 52.45% | 4.31% | 19.67% | 18.84% |

EXAMPLE 15

1-(2-bromo-6-methylphenyl)-4-methylamino-1,2-dihydro-1,3,5-triazin-2-one

To a suspension of 5.5 g (0.017 mmol) of 1-(2-bromo-6-methylphenyl)-3-methyl amidinourea in 60 ml of $CH_3CN$, there was added 5.3 ml (about 0.07 moles) of dimethyl formamidedimethyl acetal. Solid began to dissolve and a new solid precipitated. The mixture was heated to reflux and kept there for two hours. The solution remained clear on cooling to room temperature. The $CH_3CN$ was removed in vacuo and the resulting thick oil stirred in 80 ml of $H_2O$. The resulting solid was removed by filtration and washed with $H_2O$ (about 100 ml.)

The solid, after drying, was recrystallized from THF (200 ml), heated and boiled down to about 50 ml. After cooling, filtration, and washing with hexane, there was obtained 3.0 g of 1-(2-bromo-6-methylphenyl)-4-methylamino-1,2-dihydro-1,3,5-triazin-2-one melting point 238°–40° C. Analysis indicates very pure material but second crop of off-white crystals, about 2.0 g, is not as pure. The materials were combined and dissolved in hot iPA, filtered and 1.5 ml (about 0.023 moles) of $CH_3SO_3H$ added. The mixture is cooled.

The resultant solid is removed by filtrating and washed with EtOAc. The solid is recrystallized from $CH_3OH$/EtOAc to give 5.20 g of crystalline product, melting point 243°–6° C. (with decomposition).

| Calculated for: $C_{12}H_{15}BrN_4O_4$ MW: 391.23 | | | | | |
|---|---|---|---|---|---|
| | C | H | N | Br | S |
| Calculated: | 36.84 | 3.87 | 14.32 | 20.43 | 8.18 |
| Found: | 37.00 | 3.96 | 14.30 | 20.49 | 8.4 |

EXAMPLE 16

1-(2',6'-dimethylphenyl)-4-methoxyamino-1,2-dihydro-1,3,5-triazine-2-one hydrate To a suspension of 10.9 (40.0 mmol) of 1-(2,6-dimethylphenyl-3-methoxyamidinourea in $CH_3CN$ (50 ml), was added 9.5 g (80.0 mmol) of DMF-DMA and the mixture heated at 105°–110° C. in a closed bomb for 1½ hours. The reaction mixture was cooled and poured into a round bottom flask and the $CH_3CN$ removed under reduced pressure. The residue was partitioned between $CHCl_3$ and $H_2O$ and the layers separated. The aqueous layer was extracted with $CHCl_3$ (1×75 ml). The combined organic layers were washed with $H_2O$ (1×50 ml), dried ($MgSO_4$) and concentraed under reduced pressure to give an oily residue. The residue was taken up in $Et_2O$ and washed with $H_2O$ (2×50 ml). The $Et_2O$ layer was dried ($MgSO_4$) and concentrated under reduced pressure to give a viscous oil. NMR shows that DMF had been removed. The oil was taken up in hot $CH_3CN$, cooled, and a small amount of $CHCl_3$, $H_2O$, and DMSO insoluble material was filtered off. The filtrate was concentrated to give a viscous oil. TLC of the oil (Silicagel; 3% $NH_4OH$, iPA) versus starting material showed one spot which moved slower than starting material. Addition of MeOH and warming on a steam bath, the oil solidified. The solid was crystallized from MeOH to give 4.6 g (43%) of 1-(2,6-dimethylphenyl)-3-methoxyamidinourea as a white solid, melting point 78°–80° C.

| Analysis calculated for: $C_{12}H_{14}N_4O_2$ | | | |
|---|---|---|---|
| | C | H | N |
| Calculated: | 58.53 | 5.73 | 22.75 |
| Found: | 55.04 | 6.20 | 21.48 |

The NMR had shown a broad peak at 3.58 which integrated for two protons. This peak disappeared on adding $D_2O$. The analysis was recalculated for the presumed hydrate.

| Analysis calculated for: $C_{12}H_{16}N_4O$ | | | |
|---|---|---|---|
| | C | H | N |
| Calculated: | 54.54 | 6.10 | 21.20 |
| Found: | 55.04 | 6.20 | 21.48 |

Analysis indicates compound was obtained as the hydrate.

EXAMPLE 17

Therapeutic compositions of the invention are prepared by using known techniques for compounding employing either the base or a salt as the active ingredient along with the non-toxic excipients chosen in accordance with the particular form and properties desired for the therapeutic composition.

Tablets which can be advantageously used for either remedial or prophylactic treatments ordinarily accompanied by diarrhea, can be provided in a form which provides relief from diarrhea symptoms when taken at a rate of 4 to 6 tablets per day containing between about 200 to 2000 mg. of the active ingredient. An exemplary formulation which can be utilized is, for example, the following:

| | |
|---|---|
| 1-(2'6'-dimethylphenyl)-4-methylamino-1,2-dihydro-1,3,5-triazin-2-one | 500 mg. |
| tricalcium phosphate | 200 mg. |
| talc | 50 mg. |
| magnesium stearate | 10 mg. |
| polyvinyl acetate | 40 mg. |

In addition, there are added protective excipients such as ethylcellulose, dibutylphthalate, propylene glycol, wax (white and/or carbauba), spermaceti, methylene chloride, and rectified diethyl ether. The ingredients are compressed to minimum size to provide a tablet of about 850 mg.

EXAMPLE 18

A lot of 1,000 tablets each containing 1 g of 1-(2'6'-diethylphenyl)-4-methylamino-1,2-dihydro-1,3,5-triazin-2-one is prepared from the following types and amounts of ingredients:

| | |
|---|---|
| 1-(2'6'-diethylphenyl)-4-methylamino-1,2-dihydro-1,3,5-triazin-2-one | 1 kg. |
| dicalcium phosphate | 1 kg. |
| methylcellulose USP | 75 g. |
| talc | 150 g. |

| | |
|---|---|
| cornstarch | 200 g. |
| magnesium stearate | 10 g. |

The active ingredient and dicalcium phosphate are mixed thoroughly and granulated with a 7.5% solution of methylcellulose in water and passed through a #8 screen and air-dried. The dried granules are passed through a #12 screen and combined with the talc, starch and magnesium stearate with thorough mixing after which the composition is compressed into tablets.

EXAMPLE 19

A lot of 2-piece hard gelatin capsules, each containing 500 mg. of 1-(2'6'-dimethylphenyl)-4-methylamino-1,2-dihydro-1,3,5-triazin-2-one are prepared from the following types and amounts of ingredients (the amounts given are per capsule):

| | |
|---|---|
| 1-(2'6'-dimethylphenyl)-4-methylamino-1,2-dihydro-1,3,5-triazin-2-one | 500 g. |
| dicalcium phosphate | 500 g. |
| talc | 150 g. |
| magnesium stearate | 5 g. |

The ingredients are mixed thoroughly and filled into capsules which are used for oral administration at the rate of about one every four hours. If desired, slow release forms can be provided or delay release forms depending on choice of capsules and formulating ingredients.

EXAMPLE 20

A sterile solution suitable for intramuscular or interperitoneal injection, and containing 10 mg. of 1-(2'6'-dimethylphenyl)-4-methylamino-1,2-dihydro-1,3,5-triazin-2-one hydrochloride in each, 10 ml. (1:1 wt./volume), is prepared from the following ingredients:

| | |
|---|---|
| 1-(2'6'-dimethylphenyl)-4-methylamino-1,2-dihydro-1,3,5-triazin-2-one hydrochloride | 10 g. |
| benzyl benzoate | 100 ml. |
| methylparaben | 1 g. |
| propylparaben | 0.5 g. |
| cottonseed oil q.s. | 500 ml. |

EXAMPLE 21

Ten thousand tablets for oral use, each containing 50 mg. of 1-(2'6'-dimethylphenyl)-4-methylamino-1,2-dihydro-1,3,5-triazin-2-one, are prepared from the following types and amounts of material:

| | |
|---|---|
| 1-(2'6'-dimethylphenyl)-4-methylamino-1,2-dihydro-1,3,5-triazin-2-one | 500 g. |
| Lactose U.S.P. | 350 g. |
| Potato Starch U.S.P. | 346 g. |

The mixture is moistened with an alcoholic solution of 20 g. of stearic acid and granulated through a sieve. After drying, the following ingredients are added:

| | |
|---|---|
| Potato Starch U.S.P. | 320 g. |
| Talc | 400 g. |
| Magnesium stearate | 500 g. |
| Colloidal silicium dioxide | 64 g. |

The mixture is thoroughly mixed and compressed into tablets.

EXAMPLE 22

Five hundred ampoules each with two ml. of solution which contain 15 mg. of 1-(2'6'-dimethylphenyl)-4-methylamino-1,2-dihydro-1,3,5-triazin-2-one are prepared from the following types and amounts of materials:

| | |
|---|---|
| 1-(2'6'-dimethylphenyl)-4-methylamino 1,2-dihydro-1,3,5-triazin-2-one | 7.5 g. |
| Ascorbic acid | 1 g. |
| Sodium bisulphite | 0.5 g. |
| Sodium sulphite | 1 g. |

EXAMPLE 23

Capsules are prepared as follows:
15 g. of 1-(2'6'-dimethylphenyl)-4-methylamino-1,2-dihydro-1,3,5-triazin-2-one,
3 g. magnesium stearate,
2 g. of finely divided silica sold under the trademark CAB-O-SIL by Godfrey L. Cabot, Inc., Boston, Mass. and
369 g. of lactose.

The ingredients are thoroughly mixed with each other and the mixture is filled in gelatin capsules. Each capsule contains 500 mg. of the composition and thus, 15 mg. of 1-(2'6'-dimethylphenyl)-4-methylamino-1,2-dihydro-1,3,5-triazine-2-one.

EXAMPLE 24

50 g. of 1-(2'6'-dimethylphenyl)-4-methylamino-1,2-dihydro-1,3,5-triazin-2-one, 5 g. of propyl p-hydroxybenzoate are dissolved and dilluted to 5000 cc. with twice distilled water after the addition of modified Sorensen buffer solution in an amount sufficient to adjust the pH-value to a pH of 6.0. Sodium chloride is dissolved therein in an amount sufficient to render the resulting solution isotonic. The final solution is passed through a bacteriological filter and the filtrate is autoclaved at 120° C. for 15 minutes to yeild a parenterally applicable solution which contains 50 mg. of 1-(2'6'-dimethylphenyl)-4-aminomethyl-1,2-dihydro-1,3,5-triazin-2-one in 5 cc.

EXAMPLE 25

By analogous procedures, other 1,4-disubstituted-1,2-dihydro-1,3,5-triazin-2-ones can be prepared from the corresponding amidinourea starting materials, and formulated for either oral administration, as injectible or infusible solutions or for rectal administration for example, suppository form.

Illustrative compounds which can be used as active ingredients in the therapeutic compositions of this invention prepared and formulated in accordance with the methods described herein, are the following:

1-(2'6-diethylphenyl)-4-methylamino-1,2-dihydro-1,3,5-triazin-2-one
1-(2'6'-dimethylphenyl)-4-methylamino-1,2-dihydro-1,3,5-triazin-2-one-hydrochloride 1-(2'6'-dimethylphenyl)-4-methylamino-1,2-dihydro-1,3,5-triazin-2-one methanesulfonate
1-(2'6'-diethylphenyl)-4-methylamino-1,2-dihydro-1,3,5-triazin-2-one hydrochloride
4-dimethylamino-1-(2'6'-dimethylphenyl)-1,2-dihydro-1,3,5-triazin-2-one hydrochloride
1-(2-chloro-6-methylphenyl)-4-methylamino-1,2-dihydro-1,3,5-triazin-2-one
1-(2'6'-dimethylphenyl)-4-n-butoxyamino-1,2-dihydro-1,3,5-triazin-2-one
1-(2'6'-dimethylphenyl)-4-sec-butoxyamino-1,2-dihydro-1,3,5-triazin-2-one
4-methylamino-1-phenyl-1,2-dihydro-1,3,5-triazin-2-one hydrochloride
1-(2-methylphenyl)-4-ethylamino-1,2-dihydro-1,3,5-triazin-2-one
1-(2'6'-dichlorophenyl)-4-methylamino-1,2-dihydro-1,3,5-triazin-2-one
1-(2-methylphenyl)-4-methylamino-1,2-dihydro-1,3,5-triazin-2-one
1-(2'6'-dimethylphenyl)-4-(2,2,2-trifluoroethylamino)-1,2-dihydro-1,3,5-triazin-2-one
1-(2-bromo-6-methylphenyl)-4-methylamino-1,2-dihydro-1,3,5-triazin-2-one
1-(2'6'-dimethylphenyl)-4-methoxyamino-1,2-dihydro-1,3,5-triazin-2-one hydrate
1-(2'6'-diethylphenyl)-4-propylamino-1,2-dihydro-1,3,5-triazin-2-one
1-(2'6'-diethylphenyl)-4-i-propylamino-1,2-dihydro-1,3,5-triazin-2-one
1-(2'6'-diethylphenyl)-4-proparagylamino-1,2-dihydro-1,3,5-triazin-2-one
1-(2'6'-diethylphenyl)-4-cyclopropylamino-1,2-dihydro-1,3,5-triazin-2-one
1-(2'6'-diethylphenyl)-4-(N-pyrrolidinyl)-1,2-dihydro-1,3,5-triazin-2-one
1-(2'6'-diethylphenyl)-4-(N-piperidyl)-1,2-dihydro-1,3,5-triazin-2-one
1-(2'-methyl-6'-ethyl-phenyl)-4-methylamino-1,2-dihydro-1,3,5-triazin-2-one
1-(2'-methyl-6'-ethyl-phenyl)-4-(N,N-dimethylamino)-1,2-dihydro-1,3,5-triazin-2-one
1-(2'-methyl-6'-chlorophenyl)-4-methylamino-1,2-dihydro-1,3,5-triazin-2-one
1-(2'-methyl-6'-ethylphenyl)-4-(N-morpholinyl)-1,2-dihydro-1,3,5-triazin-2-one
1-(2'-methyl-6'-chlorophenyl)-4-(N-piperidinyl)-1,2-dihydro-1,3,5-triazin-2-one
1-(2'6'-dimethylphenyl)-4-[N-(3-thiomorpholinyl)]-1,2-dihydro-1,3,5-triazin-2-one
1-(2'6'-dimethylphenyl)-4-[N-(thioazolinyl)]-1,2-dihydro-1,3,5-triazin-2-one
1-(2'-chloro-6'-bromophenyl)-4-methylamino-1,2-dihydro-1,3,5-triazin-2-one
1-(2'6'-dichlorophenyl)-4-amino-1,2-dihydro-1,3,5-triazin-2-one
1-(2'-pyridyl)-4-methylamino-1,2-dihydro-1,3,5-triazin-2-one
1-(2'-peridyl)-4-ethylamino-1,2-dihydro-1,3,5-triazin-2-one
1-(3'-ethyl-pyrid-2-yl)-4-ethylene-1,2-dihydro-1,3,5-traizin-2-one
1-(3'-methyl-2-pyrid-2-yl)-4-methylamino-1,2-dihydro-1,3,5-triazin-2-one
1-(3'5'-dimethyl-pyrid-4-yl)-4-methylamino-1,2-dihydro-1,3,5-triazin-2-one
1-(2'4'-dimethyl-pyrid-3-yl)-4-methylamino-1,2-dihydro-1,3,5-triazin-2-one
1-(2'6'-dimethylbenzyl)-4-methylamino-1,2-dihydro-1,3,5-triazin-2-one
1-(2'6'-dimethylphenyl)-4-methylamino-1,2-dihydro-1,3,5-triazin-2-one

We claim:

1. A veterinary composition suitable for treating diarrhea in animals comprising an effective amount of a compound of the formula:

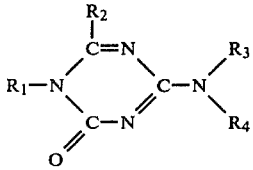

wherein $R_1$ is phenyl, benzyl or phenethyl; or phenyl, benzyl or phenethyl in which one or more of the phenyl hydrogens are substituted by lower alkyl, lower alkoxy, halo, halo-lower alkyl, amino, nitro, acyloxy, acylamino, hydroxy, cyano, carboxyl, or lower alkyl sulfonyl; pyridyl or pyridyl having one or more hydrogens replaced by lower alkyl, lower alkoxy, halo, halo-lower alkyl, amino, nitro, acyloxy, acylamino, hydroxy, cyano, carboxyl, or lower alkyl sulfonyl; $R_2$ is hydrogen or lower alkyl, and $R_3$ and $R_4$ are each independently selected from the group consisting of hydrogen, hydroxyl, lower alkanoyl, lower alkyl, lower alkenyl, lower alkynyl, lower alkoxy, halo-lower alkyl, hydroxy lower alkyl, lower alkoxy lower alkyl, phenoxy lower alkyl, di-lower alkyl-amino lower alkyl or $R_3$ and $R_4$ together with the nitrogen to which they are attached form a 5 or 6 membered nitrogen heterocycle containing 0 to 1 additional hetero atoms which may be nitrogen, oxygen, or sulfur or a non-toxic salt thereof in combination with an acceptable food carrier for administering the compound in the animal diet.

2. A composition according to claim 1 wherein the active ingredient is a compound of the formula:

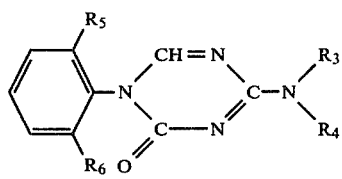

wherein $R_3$ and $R_4$ are independently selected from the group consisting of hydrogen, lower alkyl, hydroxyl, or lower alkoxy and $R_5$ and $R_6$ are each independently selected from the group consisting of hydrogen, halo, lower alkyl, lower alkoxy or halo lower alkyl and their pharmaceutically acceptable non-toxic salts.

3. A composition according to claim 2 wherein $R_3$ is hydrogen.

4. A composition according to claim 3 wherein $R_4$ is lower alkyl or lower alkoxy.

5. A composition according to claim 4 wherein each of $R_5$ and $R_6$ is lower alkyl which may be the same or different.

6. A composition according to claim 5 wherein $R_4$ is lower alkyl.

7. A veterinary composition for the treatment of diarrhea in animals comprising an effective amount of 1-(2'6'-dimethylphenyl)-4-methylamino-1,2-dihydro- 1,3,5-triazin-2-one; or a non-toxic salt thereof together with an edible food carrier.

8. A veterinary composition for the treatment of diarrhea in animals comprising an effective amount of 1-(2'6'-diethylphenyl)-4-methylamino-1,2-dihydro-1,3,5-triazin-2-one; or a non-toxic salt thereof together with an edible food carrier.

9. A method for remedial or preventive treatment of animal scours which comprises administering by oral route an effective amount of a composition comprising a compound of the formula:

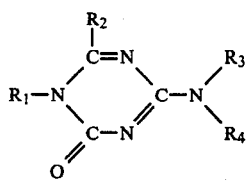

wherein $R_1$ is phenyl, benzyl or phenethyl; or phenyl, benzyl or phenethyl in which one or more of the phenyl hydrogens are substituted by lower alkyl, lower alkoxy, halo, halo-lower alkyl, amino, nitro, acyloxy, acylamino, hydroxy, cyano, carboxyl, or lower alkyl sulfonyl; pyridyl or pyridyl having one or more hydrogens replaced by lower alkyl, lower alkoxy, halo, halo-lower alkyl, amino, nitro, acyloxy, acylamino, hydroxy, cyano, carboxyl, or lower alkyl sulfonyl; $R_2$ is hydrogen or lower alkyl, and $R_3$ and $R_4$ are each independently selected from the group consisting of hydrogen, hydroxyl, lower alkanoyl, lower alkyl, lower alkenyl, lower alkynyl, lower alkoxy, halo lower alkyl, hydroxy lower alkyl, lower alkoxy lower alkyl, phenoxy lower alkyl, di-lower alkyl-amino lower alkyl or $R_3$ and $R_4$ together with the nitrogen to which they are attached form a 5 or 6 membered nitrogen heterocycle containing 0 to 1 additional hetero atoms which may be nitrogen, oxygen or sulfur; and the non-toxic salts thereof; in combination with an acceptable carrier.

10. A method according to claim 9 wherein the active ingredient is a compound of the formula:

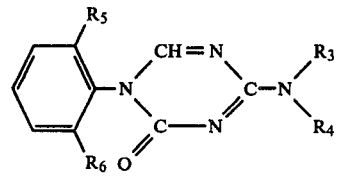

wherein $R_3$ and $R_4$ are independently selected from the group consisting of hydrogen, lower alkyl, hydroxyl, or lower alkoxy and $R_5$ and $R_6$ are each independently selected from the group consisting of hydrogen, halo, lower alkyl, lower alkoxy or halo lower alkyl and the acceptable non-toxic salts thereof.

11. A method according to claim 10 wherein $R_3$ is hydrogen.

12. A method according to claim 11 wherein $R_4$ is lower alkyl or lower alkoxy.

13. A method according to claim 12 wherein each of $R_5$ and $R_6$ is lower alkyl which may be the same or different.

14. A method according to claim 13 wherein $R_4$ is lower alkyl.

15. A method for remedial or preventive treatment of scours in food producing animals which comprises adminstering by oral route an effective amount of 1-(2'6'-dimethylphenyl-4-methylamino-1,2-dihydro-1,3,5-triazine-2-one; or an acceptable non-toxic salt thereof incorporation with a suitable carrier.

16. A method for remedial or preventive treatment of scours in food producing animals which comprises administering by oral route an effective amount of 1-(2'6'-diethylphenyl)-4-methylamino-1,2-dihydro-1,3,5-triazin-2-one; or an acceptable non-toxic salt thereof incorporated with a suitable carrier.

* * * * *